United States Patent
Driskell

(10) Patent No.: US 7,121,818 B2
(45) Date of Patent: Oct. 17, 2006

(54) SYSTEM AND METHOD FOR ABSORBENT CORE PRODUCTION

(75) Inventor: Stacy Jean Driskell, Loganville, GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 872 days.

(21) Appl. No.: 09/930,482

(22) Filed: Aug. 16, 2001

(65) Prior Publication Data
US 2003/0073968 A1    Apr. 17, 2003

(51) Int. Cl.
B27N 3/04    (2006.01)

(52) U.S. Cl. .................. 425/82.1; 425/83.1; 425/575; 222/637

(58) Field of Classification Search .............. 425/80.1, 425/82.1, 83.1, 405.1; 222/460, 574, 575, 222/637; 239/195, 589.1; D07/700
See application file for complete search history.

(56) References Cited

U.S. PATENT DOCUMENTS

| | | | |
|---|---|---|---|
| 2,589,068 A * | 3/1952 | Evans, Jr. ................ 141/98 |
| 3,544,414 A * | 12/1970 | Simison .................. 425/82.1 |
| 3,848,594 A | 11/1974 | Buell |
| 3,860,003 A | 1/1975 | Buell |
| 4,081,301 A | 3/1978 | Buell |
| 4,140,450 A * | 2/1979 | Pfeifer et al. ............ 425/82.1 |
| 4,515,595 A | 5/1985 | Kievit et al. |
| 4,610,678 A | 9/1986 | Weisman et al. |
| 4,662,875 A | 5/1987 | Hirotsu et al. |
| 4,695,278 A | 9/1987 | Lawson |
| 4,795,454 A | 1/1989 | Dragoo |
| 4,808,177 A | 2/1989 | DesMarais et al. |
| 4,816,025 A | 3/1989 | Foreman |
| 4,919,738 A | 4/1990 | Ball et al. |
| 4,938,755 A | 7/1990 | Foreman |
| 4,963,140 A | 10/1990 | Robertson et al. |
| 5,137,537 A | 8/1992 | Herron et al. |
| 5,147,345 A | 9/1992 | Young et al. |
| 5,275,590 A | 1/1994 | Huffman et al. |
| 5,281,207 A | 1/1994 | Chmielewski et al. |
| 5,326,612 A | 7/1994 | Goulait |
| 5,439,458 A | 8/1995 | Noel et al. |
| 6,123,694 A | 9/2000 | Pieniak et al. |
| 6,139,912 A | 10/2000 | Onuschak et al. |
| 6,176,952 B1 | 1/2001 | Maugans et al. |

* cited by examiner

*Primary Examiner*—Donald Heckenberg
(74) *Attorney, Agent, or Firm*—Gosz and Partners LLP

(57) ABSTRACT

A system, method, and apparatus for preparing an absorbent core for use in absorbent garments is disclosed. The apparatus includes a funnel having a first end and a second end, the second end being narrower in diameter than the first end, and a nozzle having a straight section, a curved section, and a tip. The straight section of the nozzle is operatively associated with the second end of the funnel. The apparatus further includes a diverter plate operatively associated with the curved section of the nozzle. The invention provides a more uniform distribution of super absorbent particles within the fluff pulp used to make the absorbent core, thus improving performance of the absorbent core. An absorbent garment made using an absorbent core made with the apparatus of the invention also is disclosed. The absorbent garment provides better leakage protection than absorbent garments incorporating conventional absorbent cores.

12 Claims, 5 Drawing Sheets

SYSTEM AND METHOD FOR ABSORBENT CORE PRODUCTION

FIELD OF THE INVENTION

The invention relates generally to producing absorbent cores for use in absorbent garments, and in particular to a system and method of dispensing super absorbent particles (SAP) into a stream of air with entrained fibers flowing through a forming chamber during formation of the absorbent core. Configuring the SAP nozzle, and placing it in relation to the forming chamber enables a homogenous mixture of SAP particles and fiber within the forming chamber, and ultimately the absorbent core itself. The method of the invention results in better performance of the absorbent core and the absorbent garment made using the core, as measured by standard tests for leakage. An absorbent garment that contains an absorbent core made using the apparatus and method also is disclosed.

BACKGROUND OF THE INVENTION

Disposable absorbent garments such as infant diapers or training pants, adult incontinence products, and other such products are well-known in the art. Typically, the chassis of such absorbent garments comprises a liquid-permeable body-contacting liner sheet (or "top sheet"), a liquid-impermeable backing sheet (or "back sheet"), and a moisture-absorbent core (or "absorbent core"). The absorbent core usually is made of a nonwoven mat of randomly arrayed fiber and super absorbent polymer ("SAP") and generally is disposed between the top sheet and the back sheet.

The absorbent core may be purchased as bulk roll goods or may be formed from fiberized fluff pulp and SAP particles in a forming chamber, and encased in a liquid pervious wrap to stabilize the layer or layers of the core. In the general practice of forming fibrous materials into absorbent cores, it is common to utilize a fibrous sheet of cellulosic fibers, or other suitable fibers, which is fiberized in a conventional fiberizer or other device to form discrete fibers. The discrete fibers then are entrained in an air stream or airflow along with an amount of SAP particles and directed to a forming surface where the fibers and SAP particles are deposited to form a pad of fluff, (i.e. a non-woven mat of randomly arrayed fibers containing interstitial void space and being highly compressible in character). The forming surface rotates at a speed adjusted as necessary to form the desired thickness of the pad of fluff, which is removed as a continuous sheet from the forming surface for tissue wrapping and absorbent core formation.

Typically, the air stream with the entrained discrete fibers is directed into one end of a forming chamber, where a forming surface is located on the other end of the forming chamber. The SAP particles usually are introduced into the forming chamber downstream of the point from where the discrete fibers are introduced, yet upstream of the forming surface. The SAP particles and discrete fibers mix in the air flow in the forming chamber before they reach the forming surface. The nozzle used to introduce the SAP particles into the forming chamber typically was configured to have a straight nozzle with a funnel end, and the SAP particles usually were fed into the funnel end. Typically, the funnel was disposed at about a 20 degree angle from level, or 20 degrees from a horizontal position.

The forming surface utilized in such systems typically was constructed as a wire or screen grid and typically employed pneumatic flow means such as a vacuum suction apparatus to define a differential pressure zone on the forming surface and impose a pressure differential thereon. The air entrained fiber and SAP particle stream would pass through the openings or perforations in the screened grid of the forming surface. The use of vacuum suction to draw the air entrained fiber and SAP particles stream to the forming surface, with the passage of the air component through the forming surface, is highly efficient and lends itself to high speed commercial operations. A typical configuration for feeding SAP particles to an airstream containing fibers, and then to a forming rotating drum is disclosed in U.S. Pat. No. 6,139,912, the disclosure of which is incorporated by reference herein in its entirety.

The SAP particles and the fibers typically did not mix homogeneously while inside the forming chamber to form a well-mixed pad of fluff on the forming surface, when using previous operating conditions and web forming configurations. Thus, the absorbent cores made from this pad of fluff tended to have uneven layers of SAP particles and fibers. This non-homogenous layering of the SAP particles and the fiber reduced absorbent core performance, as measured according to techniques well known in the art.

SUMMARY OF THE INVENTION

There exists a need to provide a method and apparatus for homogeneously mixing fiber and SAP particles to form an absorbent core. There also exists a need to provide absorbent cores having a more even and homogeneous distribution of SAP particles.

It would be desirable to overcome the disadvantages noted above by providing, for example, a system, method, and apparatus for dispensing SAP particles into a forming chamber during absorbent core formation such that the SAP particles mix homogenously with discrete fibers. It also would be desirable to provide uniform layers of SAP particles and fiber in a pad of fluff that ultimately results in an absorbent core made from the uniform layers in the pad of fluff, as measured by techniques such as the Z-Direction Test Protocol.

It is therefore a feature of an embodiment of the invention to provide a system, method, and apparatus to provide more homogeneous mixing of SAP particles and fiber in a forming chamber during absorbent core formation. It is another feature of an embodiment of the invention to provide a SAP nozzle configuration for introducing SAP particles into a forming chamber that results in better mixing of the SAP particles with air entrained discrete fibers. It is yet another feature of an embodiment of the invention to provide an absorbent core having homogenously mixed SAP particles and fiber, thereby resulting in improved core performance, as measured by the Strikethrough/Rewet Test Protocol. It is yet another feature of an embodiment of the invention to provide an absorbent garment assembled with an absorbent core prepared according to the procedures described above, whereby the absorbent article displays decreased leakage rates.

In accordance with these and other features of various embodiments of the invention, there are provided a system, a method, and an apparatus for dispensing SAP particles into a forming chamber. The apparatus comprises a SAP nozzle configuration for introducing the SAP particles into a forming chamber, where an airstream with entrained discrete fibers travels through the forming chamber from one end toward a forming surface located some distance from the end where the airstream enters the forming chamber. At some point between where the airstream enters the forming chamber and the forming surface, a nozzle dispenses SAP particles into the airstream to provide a substantially homogeneous mixture of discrete fibers and SAP particles. A vacuum drawn from the inside of the forming surface creates a pressure differential that draws the mixed SAP particles and discrete fibers to form a pad of fluff on the forming surface.

In accordance with another feature of an embodiment of the invention, the SAP nozzle and configuration comprise a funnel having a first end and a second end, where the second end is narrower in diameter than the first end. The nozzle further contains a straight section, a curved section, a tip, and a diverter plate. One end of the straight section of the nozzle is associated with the second end of the funnel, and the other end of the straight section is associated with one end of the curved section. The diverter plate is associated substantially with the other end of the curved section of the nozzle, and the diverter plate preferably extends beyond the end of the curved section and the tip of the nozzle. The diverter plate may be angled in relation to the tip of the nozzle, with the tip of the nozzle substantially flush against the diverter plate.

In accordance with another feature of an embodiment of the invention, there is provided an absorbent core assembled from a pad of fluff made using the SAP nozzle and configuration described above. The absorbent core demonstrates a uniform mixture of SAP particles and discrete fibers, resulting in decreased Strikethrough times and Rewet weights, as measured by standard techniques known in the art.

In accordance with another feature of an embodiment of the invention, there is provided an absorbent garment having a top sheet material, a bottom sheet material, and an absorbent core disposed between the top sheet material and the bottom sheet. The absorbent core is made from the pad of fluff formed using the SAP nozzle and system of the invention.

BRIEF DESCRIPTION OF THE DRAWINGS

The invention will be described with reference to the accompanying drawings, in which like elements are referenced with like numerals.

DETAILED DESCRIPTION OF PREFERRED EMBODIMENTS

Figure 1:
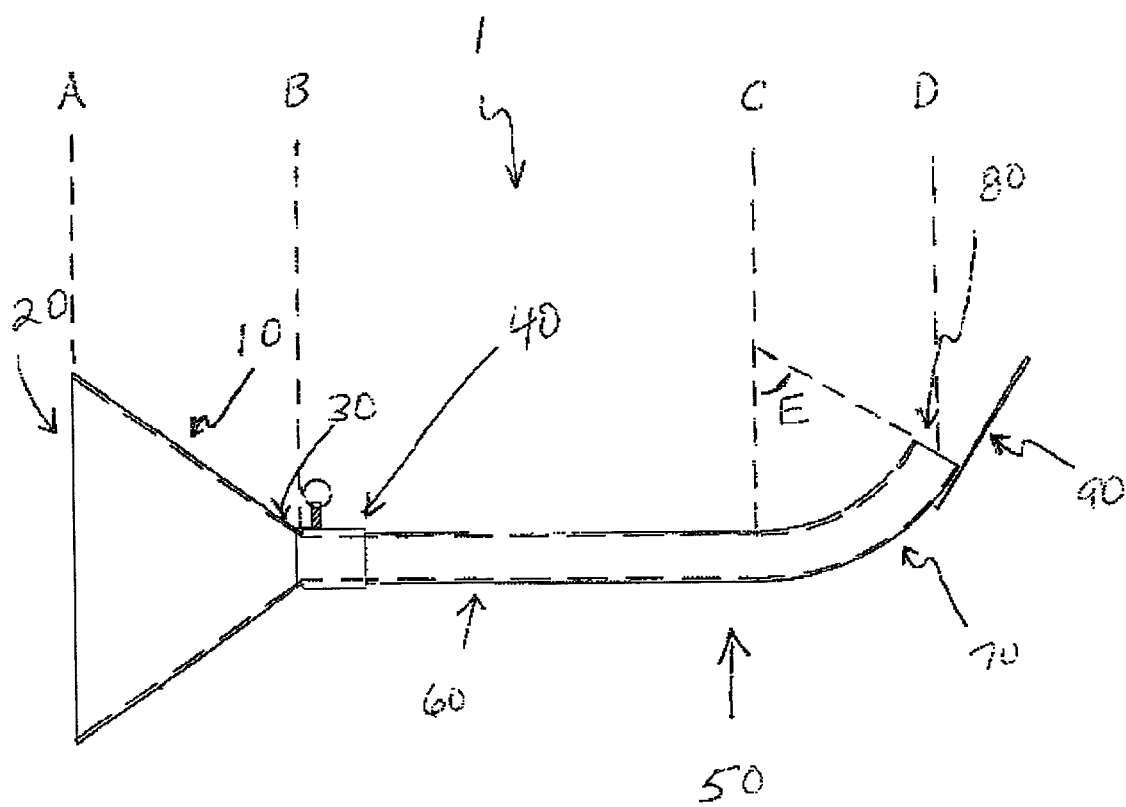
FIG. 1 is a schematic of a SAP nozzle according to an embodiment of the invention.

Throughout this description, the expression "Absorbent garment," refers to articles and garments that absorb and contain body exudates, and more specifically refers to articles and garments that are placed against or in proximity to the body of the wearer to absorb and contain the various exudates discharged from the user's body. A non-exhaustive list of examples of "absorbent garments" and garments includes diapers, diaper covers, disposable diapers, training pants, feminine hygiene products, and adult incontinence products. The invention can be used with all of the foregoing classes of absorbent garments and garments, without limitation, whether disposable or otherwise. Furthermore, the invention will be understood to encompass, without limitation, all classes and types of absorbent garments and garments, including those described above.

Although the various embodiments of the invention are described in the context of a diaper, it is readily apparent and understood that this is not intended to limit the invention.

The term "Strikethrough" is used herein to denote the amount of time it takes for liquid to pass through the material being tested. Strikethrough is a measure of the fluid acquisition properties of the material. Strikethrough is measured in accordance with the test procedures defined in the examples below. Unless indicated otherwise, Strikethrough values are reported herein in seconds.

The term "Rewet" is used herein to mean retransmission of liquid from the absorbent core to the body or wearer side of the topsheet when the disposable absorbent article is in use. Rewet therefore is a measure of the absorbent article's fluid retention capabilities under load. Low Rewet means low retransmission of liquid from the absorbent core to the body or wearer side of the topsheet. The Rewet property of an absorbent article is determined by the procedure outlined in the test procedures defined in the examples below. Unless indicated otherwise, Rewet values are reported herein in ml.

As mentioned above, the invention strives to overcome the disadvantages noted above by providing, for example, a system, method, and apparatus for dispensing SAP particles into a forming chamber during absorbent core formation such that the SAP particles mix homogenously with discrete fibers. The invention also provides uniform layers of SAP particles and fiber in a pad of fluff that ultimately results in an absorbent core made from the uniform layers in the pad of fluff, as measured by techniques such as the Z-Direction Test Protocol. The Z-Direction Test Protocol is described in more detail below in the examples. It is believed that this homogeneity results in improved core performance as noted, for example, by a decrease in the Strikethrough time, and a decrease in the amount of Rewet of the absorbent cores. Additionally, the invention provides absorbent garments made with absorbent cores having a more uniform fiber and SAP particle distribution, which has been prepared using the SAP nozzle configuration. These absorbent articles display demonstrably less leakage as seen in home use tests of the absorbent garments.

One advantage of the invention is a homogeneous mix of fiberized fluff pulp and SAP particles in an absorbent core formed according to the invention, resulting in improved performance of the core. Another advantage of the invention is an economical use of SAP, which is a major cost in a finished absorbent article. Better mixing of the SAP particles with the fiberized fluff pulp in the absorbent core provides an improved absorbent garment for the same cost as formerly known lower performance absorbent garments, thus providing better value for the same cost of SAP.

The invention preferably is a system, a method, and an apparatus for dispensing SAP particles into a forming chamber. The apparatus includes a particularly preferred SAP nozzle configuration for introducing the SAP particles into a forming chamber. An airstream having discrete fibers entrained therein travels through a forming chamber (e.g., a web forming chamber) from one end toward a forming surface located some distance from the end where the airstream enters the forming chamber. The forming surface preferably is located on the surface of a rotating drum. At some point between the point where the airstream enters the forming chamber and the forming surface, a nozzle dispenses SAP particles into the airstream to provide a substantially homogeneous mixture of discrete fibers and SAP particles. A vacuum drawn from the inside of the forming surface creates a pressure differential that draws the mixed SAP particles and discrete fibers to form a pad of fluff on the forming surface.

The SAP nozzle and configuration preferably includes a funnel having a first end and a second end, where the second end is narrower in diameter than the first end. Accordingly, the first end of the funnel has a diameter larger than the second end, which enables the introduction of SAP particles into the funnel. It is preferred that the SAP particles are free flowing granular materials capable of being easily transported through the funnel and nozzle. The nozzle further contains a straight section, a curved section, a tip, and a diverter plate. One end of the straight section of the nozzle is associated with the second end of the funnel, and the other end of the straight section is associated with one end of the curved section. The diverter plate is associated substantially with the other end of the curved section of the nozzle, and the diverter plate preferably extends beyond the end of the curved section of the nozzle. The diverter plate preferably is angled in relation to the tip of the nozzle, with the tip of the nozzle substantially flush against the diverter plate.

FIG. 1 is a schematic view of a SAP nozzle 1 according to an embodiment of the invention. The SAP nozzle 1 may have a funnel end 10 and a nozzle end 50 with a straight section 60 and a curved section 70. The tip 80 may be blunt as depicted in FIG. 1, although in other embodiments the tip 80 may taper to a point (not shown). The funnel end 10 may have a wide mouthed end 20 for loading the SAP particles for feeding into the SAP nozzle 10, and a narrow mouthed end 30 operatively attached to the straight section 60 of the SAP nozzle 50. In the pictured embodiment, the funnel end 10 is attached to the nozzle end 50 using a clamp 40 tightened with a thumb screw, although the funnel end 10 may be attached to the nozzle end 50 by any attachment means now known or later developed, appropriate to the construction material of the nozzle. In yet other embodiments, the funnel end 10 and the nozzle end 50 may be of unitary construction. The manner of attachment is not material to the invention, however, so long as the funnel 10 and nozzle 50 remain intact during operation. Those skilled in the art are capable of attaching funnel end 10 and nozzle 50 using techniques known in the art.

The SAP nozzle may have a diameter of about one (1) inch, but may be adjusted as necessary to provide the necessary flow of SAP particles required to provide the quantity of SAP particles in the pad of fluff being formed in the forming chamber. Skilled artisans are capable of varying the diameter of the SAP nozzle to provide for more rapid or slower flow of SAP particles, as desired, depending on the desired rate of application, and the size and morphology of the particles.

A diverter plate 90 preferably is attached to one end of the curved section 70 of the nozzle by any means now known or later developed. For example, the diverter plate 90 in one embodiment may be welded to one end of the curved section 70. In other embodiments, support structures may be welded to the nozzle 50 and the diverter plate 90 for attachment purposes. In yet other embodiments, the diverter plate 90 may be attached to one end of the curved section 70 of the nozzle in such a manner that the angle of the diverter plate 90 in relation to the tip of the nozzle 80 may be adjusted to provide the best performance for the mixing of SAP particles with the fiberized fluff pulp in the forming chamber. The angle of the diverter plate may be from approximately a 10 degree angle to approximately a 70 degree acute angle, where the angle is measured between a hypothetical plane extending beyond the tip of the nozzle if the diverter plate were straight and un-bent, and the bent diverter plate. The bent diverter plate preferably is angled in the direction of the tip of the nozzle 80, and the tip of the nozzle 80 preferably is substantially located at a right angle, and more preferably, at an obtuse angle of about 150 degrees or greater. The manner of attachment is not essential to the invention, and any mechanism capable of attaching diverter plate 90 to nozzle 50 would be sufficient for the present invention.

Figure 2:
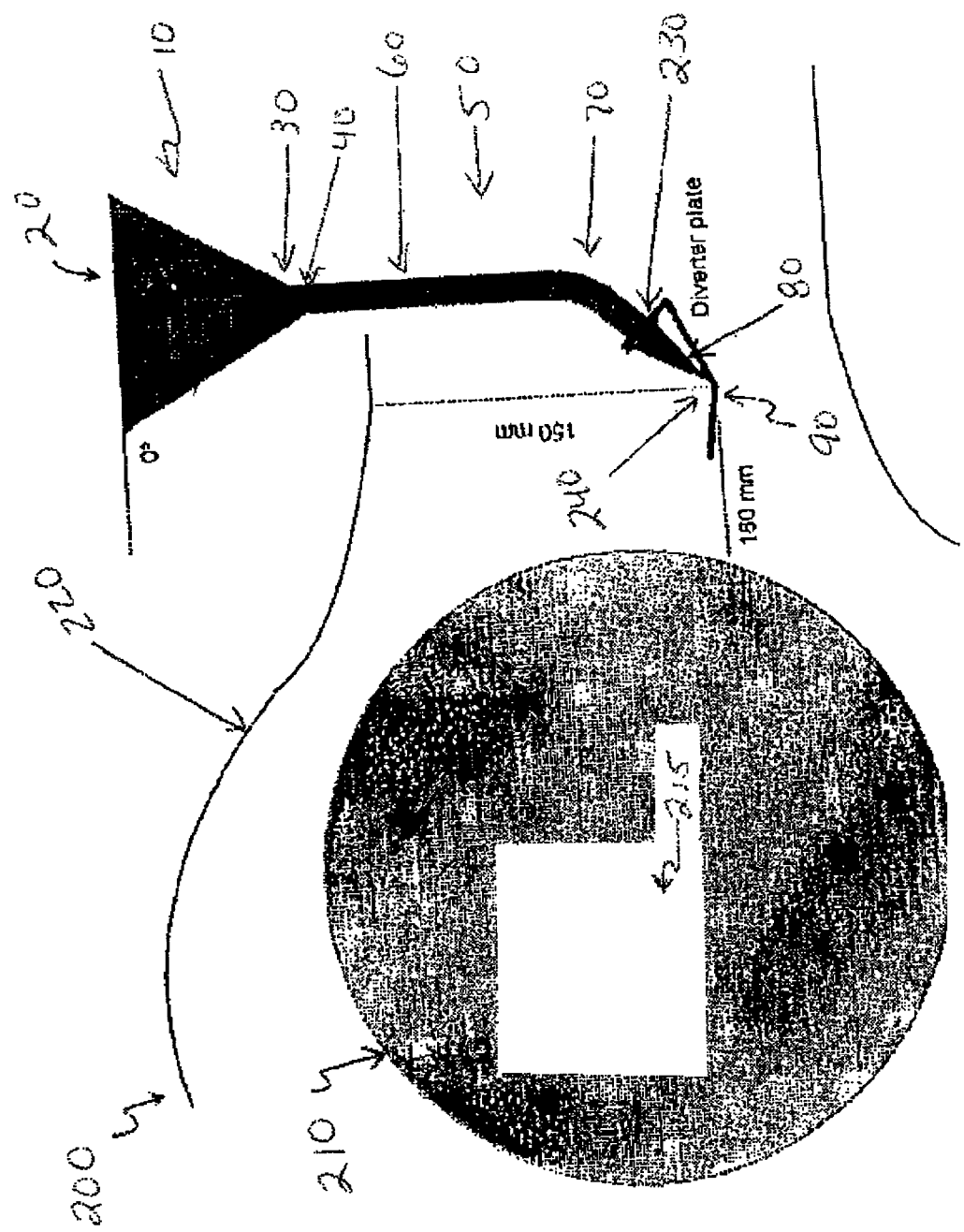
FIG. 2 is a schematic of a SAP nozzle as it is configured in relation to the forming chamber according to an embodiment of the invention.

FIG. 2 is a schematic of the SAP nozzle as it is configured in an embodiment of the invention. As shown in FIG. 2, SAP nozzle 50 is shown in relation to the forming chamber 200. The forming chamber 200 preferably has an upper section 220 through which the SAP nozzle 50 protrudes into the forming chamber 200. A forming surface 210 is located at one end of the forming chamber 200, and typically has a wire or screened surface, although it may be comprised of any type of surface including a perforated steel drum-like surface. A stream of air with entrained discrete fibers (not shown) preferably enters the forming chamber 200 at a distance from the forming surface 210, and a pneumatic flow mechanism 215 draws the flow of air in the forming chamber 200 through the forming surface 210, causing the entrained discrete fibers and SAP particles to deposit on the forming surface 210.

The wider-mouthed end 20 of the funnel 10 preferably is level, or at or about 0 degrees with respect to horizontal, as shown in FIG. 2. The tip 80 of the nozzle 50 may be placed about 155 mm to about 205 mm, and more preferably about 180 mm horizontally from the forming surface 210. Tip 80 also preferably protrudes about 140 mm to about 160 mm, and more preferably about 150 mm below the surface of the upper section 220 (preferably made of, for example, plexiglas, or the like) and into the forming chamber 200. Once the nozzle 50 is properly located, the diverter plate 90 may be installed. Skilled artisans are capable of properly locating nozzle 50 in forming chamber 200, using the guidelines provided herein.

In the embodiment shown in FIG. 2, the tip 80 of the curved section 70 of the nozzle 50 tapers to form a point. The diameter of the tip of the nozzle 80 can range anywhere from the diameter of the curved section 70 of the nozzle 50 to a size that does not impede the flow of the SAP particles into the forming chamber 200. The diverter plate 90 preferably is attached to the nozzle 50 by a welded collar 230 that is located at or near the end of the curved section 70 of nozzle 50, and more preferably, at the point the curved end 70 of the nozzle 50 begins to taper to form the tip 80, as shown in FIG. 2. The tip 80 of the nozzle should sit flush against the inside surface of the angle 240 of the diverter plate 90.

Figure 3:
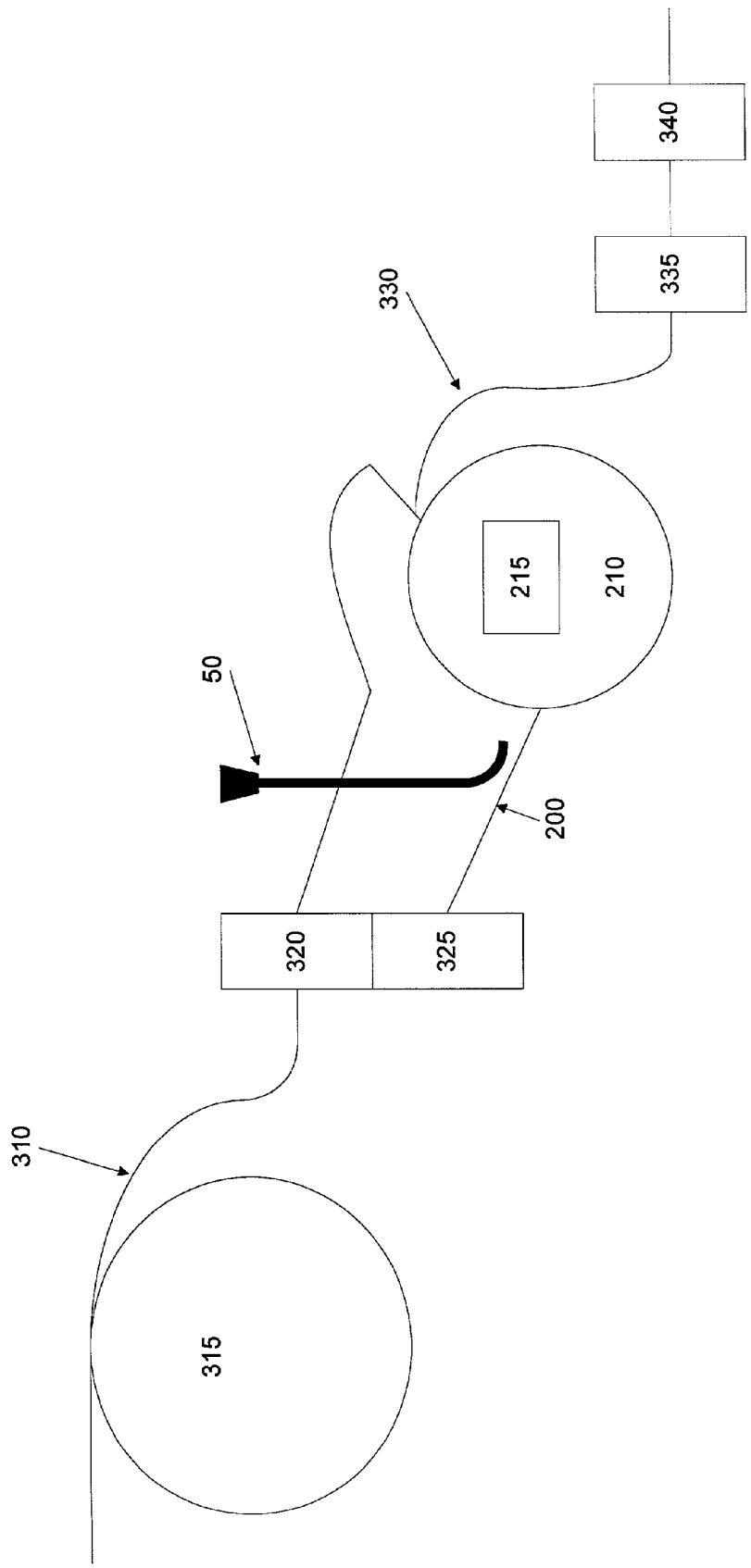
FIG. 3 is a schematic of an embodiment of the invention of a system for introducing SAP particles into a forming chamber to form a uniformly mixed pad of fluff used for making absorbent cores.

FIG. 3 is a schematic of one embodiment of the invention pertaining to a system for introducing SAP particles into a forming chamber using the SAP nozzle and configuration to form a uniformly mixed pad of fluff for making absorbent cores. Adding SAP to pulp fibers formed into a foraminous web generally is known and described in, for example, U.S. Pat. No. 6,139,912, the disclosure of which is incorporated by reference herein in its entirety. Fibrous sheets of pulp 310 may be unwound using a pulp unwinding wheel 315, or other type of unwinding apparatus 315, and continuously supplied to a fiberizer 320 where the sheets are fiberized to form discrete fibers. The discrete fibers then preferably are entrained in an air flow stream from, for example, a fan 325, which is directed into one end of a forming chamber 200. In one preferred embodiment, the forming chamber 200 may be made of Plexiglas. The air containing the entrained discrete fibers preferably enters forming chamber 200 at a speed adjusted as necessary to provide the desired thickness of pad of fluff according to assembly conditions. Alternatively, a vacuum suction apparatus 215 may create enough suction to negate the need for fan 325. Those persons having ordinary skill in the art are capable of designing a suitable air flow mechanism (e.g., either by blowing air, sucking air, or various combinations of each) to provide for sufficient and variable air flow for forming the desired thickness of fluff.

A forming surface 210 preferably is disposed at a point in the forming chamber 200 distant from the end where the air containing entrained fibers is introduced, and preferably, is disposed at the opposite end of chamber 200. Forming surface 210 can be a slowly rotating drum or wheel whose surface is comprised of a screen, a wire grid, a perforated steel plate, or any other suitable forming surface 210 capable of forming a web of fibers thereon. A vacuum suction apparatus 215 preferably is used to draw a vacuum through the forming surface 210, which has holes or perforations to allow air to pass there through, but not allow a substantial amount of entrained fibers or SAP particles.

SAP nozzle 50 preferably is disposed at a point between where the air stream containing the entrained discrete fibers enters the forming chamber 200 and the forming surface 210. SAP nozzle 50 introduces SAP particles into the forming chamber 200 to be mixed with the entrained discrete fibers before the air stream exits through the screen or wire grid of the forming surface 210. Thus, the SAP particles are mixed with the fibers prior to the fibers and SAP particles being disposed on forming surface 210, which results in a more homogeneous mixing of the fibers and SAP particles. The pressure differential caused by the vacuum suction apparatus 215 can draw the discrete fibers and SAP particles to the forming surface 210 to form a pad of fluff 330 on the forming surface 210.

The forming surface 210 may rotate at a speed adjusted as needed to form the thickness of the pad of fluff desired, preferably from around 45 feet per minute to around 60 feet per minute. Those skilled in the art are capable of determining a suitable rotation speed for forming surface 210 to provide the desired thickness and consistency of the pad of fluff 330. The pad of fluff 330 can be continuously removed from the forming surface 210 and conveyed directly to an absorbent article forming apparatus, (not shown), or prior to forming the absorbent article, it can be conveyed to a tissue folding unit 335 (FIG. 3) where it can be wrapped in moisture-permeable tissue. The tissue also maintains the integrity of the pad of fluff. The wrapped pad of fluff 330 then may continue to a press roll unit 340 to be pressed and formed into an absorbent core. The formed absorbent cores then can be conveyed along a belt to be assembled into finished absorbent garments.

Figure 4:
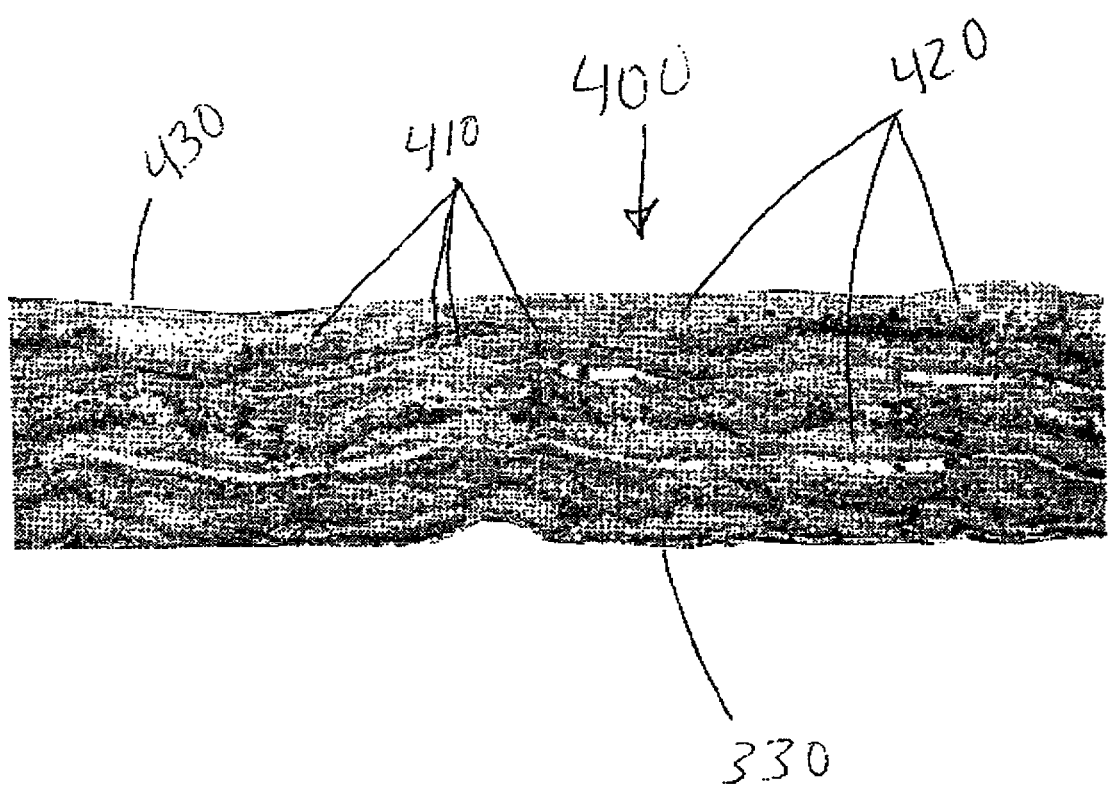
FIG. 4 is a schematic view of an absorbent core made according to an embodiment of the invention.

FIG. 4 is a cut away schematic view of an absorbent core 400 made in accordance with an embodiment of the invention, as would be observed according to the Z-Direction Test Protocol described in more detail in the examples below. The absorbent core 400 may comprise a moisture permeable tissue 430 encasing a pad of fluff 330 made according to the invention from a mixture of discrete fibers 410 and SAP particles 420. The SAP particle distribution within the discrete fibers in the absorbent core are noted by the darkened areas in the schematic, as would be observed after staining with a bromocresol purple solution in the Z-Direction Test Protocol.

Figure 5:
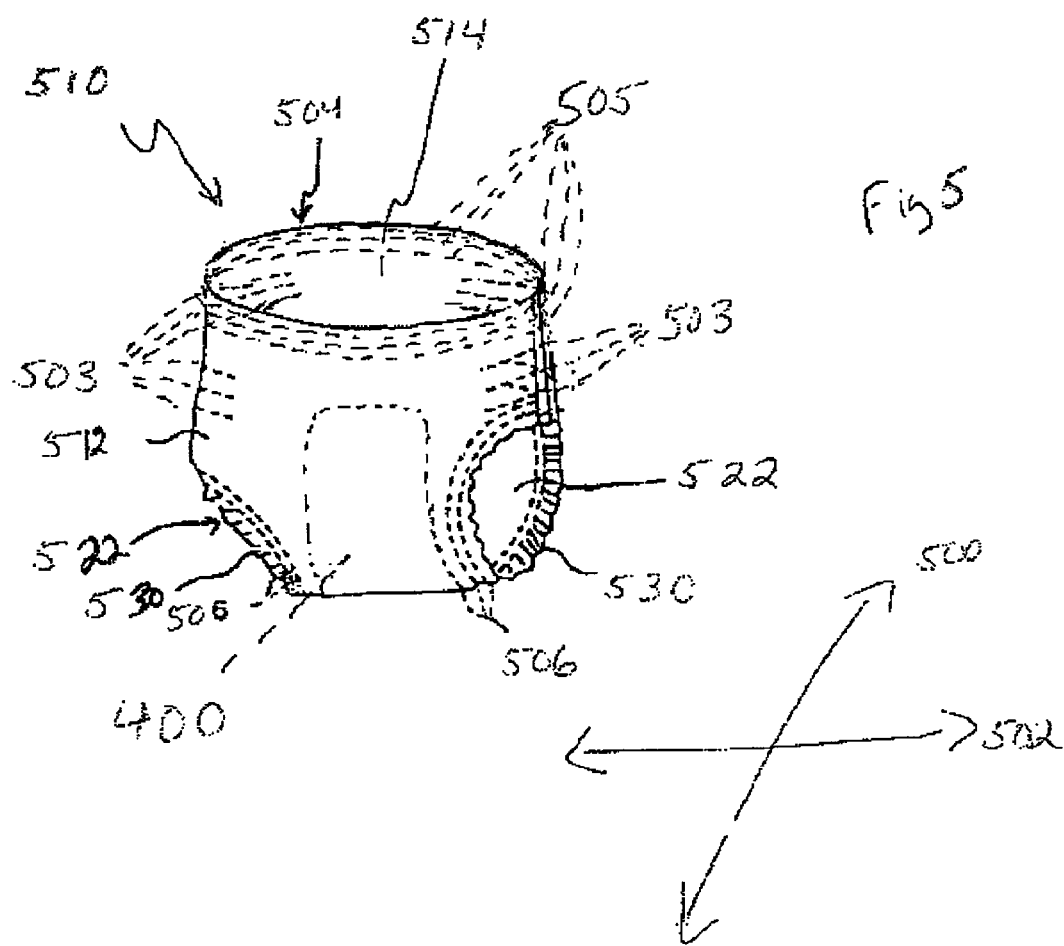
FIG. 5 is a schematic view of an absorbent garment that incorporates an absorbent core made according to an embodiment of the invention.

FIG. 5 depicts an embodiment of an absorbent garment incorporating the absorbent core made according to the invention as it appears when worn by a user. The garment 510 has a longitudinal axis 500 corresponding approximately to the rear-to-front axis of the wearer, and a lateral axis 502, orthogonal to the longitudinal axis 500, and corresponding approximately to the side-to-side axis of the wearer. In the depicted embodiment, the garment 510 is comprised of a main body having an exterior facing moisture impervious outer layer 512 or "back sheet," and a moisture pervious body-contacting inner layer 514 or "top sheet." The absorbent core 400 typically is disposed between the top sheet 514 and the back sheet 512. Each of the back sheet, top sheet, and absorbent core may comprise a plurality of layers of materials that, once assembled, can generally be considered a unitary element of the garment. In addition, a transfer layer (not shown) may be disposed between the top sheet 514 and the absorbent core 400, and a barrier film (not shown) may be disposed between the absorbent core 400 and the back sheet 512. In the embodiment depicted in FIG. 5, the back sheet 512, top sheet 514, and absorbent core 400 comprise the main body of the garment. In another embodiment of the invention, however, the main body may be made from a separate sheet (not shown) and the back sheet 512, top sheet 514, and absorbent core 400 may be assembled separately and then attached to the main body.

The back sheet 512 may comprise a laminate of multiple layers of materials that have similar or different properties, but are preferably made from a substantially liquid impervious material. The selection and manufacture of such materials is well known in the art, and is disclosed, for example, in U.S. Pat. No. 6,123,694 issued to Peniak et al., and U.S. Pat. No. 6,176,952 issued to Maugans et al., each of which is incorporated herein by reference in its entirety, and in a manner consistent with the present invention. In one embodiment, the back sheet 512 is made from a thin thermoplastic material, such as a pigmented polyethylene film having a thickness in the range of 0.02–0.04 mm, and may also have a laminate construction comprising one or more layers of meltblown polypropylene or meltblown polyethylene, sandwiched between layers of spun-bonded material (often referred to as an "SMS" laminate). Additional layers may be added in order to provide the back sheet 512 with other desirable properties, such as to improve the tactile feel, or "hand." The back sheet 512 may also be entirely or partly gas pervious to allow the garment to circulate air, or "breathe."

The back sheet 512 may define the outer perimeter of the main body of the garment, such that no other parts of the garment 510 extend beyond the outline of the back sheet 512 when the main body of the garment is laid flat. However, in other embodiments the back sheet 512 may not define the outer perimeter of the garment, and other parts may extend beyond the edges of the back sheet 512.

The top sheet 514, which preferably overlays the back sheet 512, can be made from a substantially liquid pervious material to allow body exudates to penetrate into the absorbent core 400. The top sheet 514 may typically be comprised of a carded polyester fiber with a latex binder or of a spun-bonded polypropylene having continuous fibers and thermally bonded by patterned calendar rolls. The top sheet 514 may be treated over all or part of its surface to render it hydrophilic, and may also be zone-treated with a surfactant to render it hydrophilic only in certain target areas. The top sheet 514 also may be treated with skin treating ingredients, such as aloe, vitamin E, and the like, which can be accomplished by a variety of methods known in the art. The top sheet 514 may also comprise an apertured material, such as an apertured film.

In one embodiment of the present invention, the top sheet 514 may comprise a laminate of several layers of material, which may have different physical properties. In another embodiment, the top sheet 514 is made from several pieces of material joined at or near their edges with little or no overlap, which may have dissimilar physical properties (multi-panel construction). Such an embodiment is disclosed, for example, in U.S. Pat. No. 5,275,590 issued to Huffman et al., which is incorporated herein by reference in its entirety, and in a manner consistent with the present invention.

In one embodiment of the invention, the top sheet 514 has a different shape and size than the back sheet 512. In other embodiments, the top sheet 514 may have substantially the same planar dimensions as the back sheet 512, such that the perimeter of the top sheet 514 matches the perimeter of the back sheet 512. In one embodiment, the top sheet 514 is large enough to completely cover all of the parts of the garment that are sandwiched between the top sheet 514 and the back sheet 512, such as the absorbent core 400, the transfer layer (not shown), and the barrier film (not shown).

In one embodiment of the invention, the top sheet 514 and the bottom sheet 512 are comprised of a nonwoven material. The top sheet 514 and bottom sheet 512 may also be made, however, from any other suitable material. In one embodiment, the top sheet 514 and bottom sheet 512 are selected to provide a good tactile impression, or "hand," to provide a comfortable fit. In another embodiment of the invention, the top sheet 514 and bottom sheet 512 are selected to be gas permeable to improve the breathability of the garment 510. In yet another embodiment of the invention, the top sheet 514 and bottom sheet 512 are comprised of materials having different physical properties.

In one embodiment of the present invention, where the top sheet 514 has substantially similar dimensions to the back sheet 512, the top sheet 514 and back sheet 512 may be bonded to one another in substantially all areas not having intermediately placed parts, such that some or all of the intermediately placed, or "sandwiched," parts are physically captured between the top sheet 514 and back sheet 512, but not bonded to the back sheet 512 or top sheet 514. In this embodiment, the absorbent core 400 preferably is disposed between the inner surfaces of the back sheet 512 and the top sheet 514. In other embodiments, where the top sheet 514 and back sheet 514 do not have the same dimensions, the top sheet 514 may be disposed between nonwoven strips (not shown) and the back sheet 512, and the nonwoven strips (not shown) would be operatively associated with the back sheet 512 substantially around the waist area 504 of the back sheet 512 in a lateral direction 502. In this embodiment, the nonwoven strips (not shown) and back sheet 512 may be operatively associated with one another by using hot melt adhesives, ultrasonic bonding, or any other suitable method known in the art.

The absorbent core 400 may be comprised of one or more layers of material, such as an absorbent layer for storing fluids and an acquisition layer for distributing fluids. Such multiple layer absorbent cores are known in the art and disclosed in U.S. Pat. No. 5,439,458 issued to Noel et al., which is incorporated herein by reference in its entirety, and in a manner consistent with the present invention.

The absorbent core 400 may be made from any absorbent material or materials known in the art. In one embodiment of the invention, the absorbent core 400 comprises wood fibers or other fibers such as chemical wood pulp, fibrous absorbent gelling material, or any other suitable liquid absorbing material, such as commercially available fluff pulp or fluffed bleached kraft softwood pulp or fibrous absorbent gelling material. In another embodiment of the invention, the absorbent core 400 comprises a combination of a porous fibrous web and super absorbent particles. Absorbent cores are known in the art and are disclosed, for example, in U.S. Pat. No. 5,281,207 issued to Chmielewski et al., U.S. Pat. No. 4,610,678 issued to Weisman et. al., U.S. Pat. No. 5,137,537 issued to Herron et. al., and U.S. Pat. No. 5,147,345 issued to Young et. al., which are incorporated herein by reference in their entirety, and in a manner consistent with the present invention. In such an embodiment, the absorbent core 400 may be surrounded by a liquid pervious tissue over-wrap, or other material.

The absorbent core 400 generally is elongated along the longitudinal axis 500 of the garment, and may extend along either or both of the lateral and longitudinal axes 502, 500 to the outer perimeter of the garment. In the embodiment depicted in FIG. 5, the absorbent core 400 is substantially rectangular in shape, however, it may also have rounded ends or other shapes, such as an "I" shape or a "T" shape. The absorbent core 400 may also have channels, grooves or pockets, and may have a varying thickness.

The garment 510 of the present invention may include various mechanisms for improving the fit to the wearer, and for improving leakage resistance. In the embodiment of the present invention depicted in FIG. 5, the garment 510 further comprises various mechanisms for improving the ability of the garment 510 to contain body exudates, such as conventional leg gathers 530. Such gathers, formed by incorporating a plurality of elastic elements 506 with the top sheet 514 and bottom sheet 512 in the leg hole area 522, contract the leg holes 522 around the wearer's legs in the upper thigh area to prevent leakage. Alternatively, and in addition, standing leg gathers (not shown) may be formed by incorporating a plurality of elastic elements 506 into elements (not shown) that are then associated with the top sheet 514 and bottom sheet 512 in the leg hole area 522. U.S. Pat. Nos. 3,860,003 and 4,081,301 issued to Buell, U.S. Pat. No. 4,695,278 issued to Lawson, U.S. Pat. No. 4,808,177 issued to Des Marais, U.S. Pat. No. 4,795,454 issued to Dragoo, and U.S. Pat. No. 4,938,755 issued to Foreman illustrate other embodiments of leg cuffs in absorbent garments, and the disclosures of each of these patents are hereby incorporated by reference in their entirety.

The absorbent garment 510 incorporating the present invention may further comprise elastic elements 505 in the waist area 504, and/or elastic elements 503 in other portions of the main body to improve the fit of the garment. In one embodiment, one or more elastic elements 505 may be extended and bonded to the back sheet 512 substantially in the waist area 504 of the garment 510. U.S. Pat. No. 4,515,595 issued to Kievit et. al. and U.S. Pat. No. 4,816,025 issued to Foreman illustrate other embodiments of elasticized waist features of absorbent garments, and are hereby incorporated by reference in their entirety. Also, one or more elastic elements 503 may be extended, disposed between, and bonded to the back sheet 512 while the elastic is in the extended state.

When the elastic elements 503, 505, and 506 contract after bonding, the parts of the garment to which the elastic elements are attached constrict, or "shirr," causing the garment to form to the wearer's body. The elastic elements 503, 505, and 506 may be made from natural rubber, LYCRA®, polyurethane, heat shrinkable polymer ribbons, or any other suitable elastic material or composite.

In other embodiments, adjustment strips (not shown) may be disposed on and partially attached to the garment to provide for an adjustable fit. Absorbent garments often loosen during use for various reasons, such as inelastic stretching of the various components, changes in user size, and increased loading caused by the release of body exudates into the garment 510. The attachment strips may be formed such that they may be releasably attached directly to the main body of the garment, the back sheet 512, or to an adjuster attachment area, and may comprise cloth, film, nonwoven material, or any other suitable material. It is readily understood to one skilled in the art that any suitable attachment methods may be used to connect the adjustment strip to the main body of the garment. U.S. Pat. No. 3,848,594 issued to Buell, Re B1 U.S. Pat. No. 4,662,875 issued to Hirotsu et. al., U.S. Pat. No. 5,326,612 issued to Goulait, and U.S. Pat. No. 4,963,140 issued to Robertson et. al. illustrate fasteners for absorbent garments, and the disclosures of each are herein incorporated by reference in their entireties.

The various parts of the garment 510 preferably are operatively associated with one another in such a manner that the garment will maintain its desired structure during use. The parts may be operatively associated with one another by a variety of methods known in the art, including, but not limited to: using adhesives such as hot melt adhesives and construction adhesives, chemical or solvent bonding, ultrasonic welding, stitching, heat bonding, autogenous bonding, or any other method of affixation known or hereafter discovered. U.S. Pat. No. 4,919,738 issued to Ball et. al. discloses a method of autogenous bonding, and its disclosure is herein incorporated by reference in its entirety in a manner consistent with the invention. All of the parts may be joined to each adjacent part, but some parts may not be joined to others. In one embodiment, the top sheet 514 and back sheet 512 are bonded to one another around their perimeter regions, thereby encasing and holding the absorbent core 400 in place without having to directly join the absorbent core 400 to any parts of the garment 510. The top sheet 514 or back sheet 512 may also be directly operatively associated with the absorbent core 400. As understood herein, the term "operatively associated" includes directly joining one part to another, indirectly joining parts together through one or more intermediary parts, whether those intermediary parts are described herein or not, joining parts in such a manner that unjoined parts are captured or held in their proper place, and any other suitable joining means that maintains the structural integrity of the garment 510 for the duration of its use.

The invention is further illustrated by the following Examples which should not be regarded as limiting.

EXAMPLE 1

The following testing procedures were used to analyze the absorbent cores made in accordance with the various examples (comparative and inventive) below.

Z-Direction Test Protocol

The Z-Direction Test Protocol is a test to analyze the distribution of SAP particles in an absorbent core. The width of an absorbent core is measured from side to side, and the center point is determined. A center line is drawn from end to end, and the core is sliced open lengthwise. With the back of the absorbent core toward the tester, the left half is discarded. The right half is tested, with the top sheet material facing up.

For testing, a 0.4 wt. % bromocresol purple solution in deionized water is prepared from powdered bromocresol purple. For example, 0.24 gm of bromocresol purple powder would be added to a 600 ml spray bottle, and sufficient deionized water would be added until the contents of the spray bottle weighed 600 gm. With the cut half of the absorbent core facing the tester, top sheet material facing up, the core material is sprayed with the 0.4 wt. % bromocresol purple solution until the SAP particle distribution can clearly be seen, as the SAP particles turn deep purple and the fiber turns yellow in the testing solution.

The SAP particle distribution is observed, and photographed from a distance of approximately two (2) feet. A subjective description of the distribution according to the tester also is noted.

A somewhat modified Z-Direction Test Protocol also was conducted, whereby the absorbent cores were cut in a cross direction across the width of the core to detect any narrowing of the SAP distribution along the width of the core. Thus, the cores were cut along their width, orthogonal to the lengthwise cut used in the Z-Direction Test Protocol Test described immediately above. An identical test solution was used, and the samples were observed, photographed, and described as detailed before.

Strikethrough/Rewet Test Protocol

The Strikethrough/Rewet Test Protocol determines the Strikethrough time, in seconds, and the amount of Rewet, in gm, for an absorbent garment. The Strikethrough time indicates how quickly free liquid is taken into the absorbent core, and the Rewet weights indicate how much free liquid will come back out of the absorbent core after a particular time period. A synthetic urine solution is used in the Strikethrough and Rewet tests, and can be prepared as follows. First, about 10 gm of Triton X-100® (polyethylene glycol octylphenol ether) are measured into a 1000 ml flask, which then is filled to 1000 ml with deionized water to make a 1 wt. % Triton X-100 solution. Then, about 100 g of the 1 wt. % Triton X-100 solution prepared above, and about 360 gm of NaCl are added to a 40 liter container, and diluted to 40 liters with deionized water to make the test solution.

The side seams of an absorbent garment are split open, and the garment is stretched with the top sheet material facing up. The center of the core is determined and marked, and a strikethrough plate is placed directly over the center point. The strikethrough plate preferably is a transparent acrylic sheet with an open top for receiving test solution, an interior cavity capable of retaining the test solution while it is absorbed into the absorbent core, and an exit port located substantially adjacent to the absorbent core for the test solution to exit the strikethrough plate and be absorbed by the absorbent core being tested. About 100 ml of the test solution are placed in a separatory funnel, which is placed a few mm over the center point of the absorbent core. The separatory funnel is opened, and a timer is simultaneously started. The cavity of the strikethrough plate should be maintained completely full of test solution to keep a constant pressure over the absorbent core. When all of the test solution has been absorbed into the absorbent core, the timer is stopped giving the Strikethrough time in seconds.

The Rewet weight is determined by removing the strikethrough plate from the absorbent core and placing a 0.5 psi weight onto the wetted sample, which remains in place for 10 minutes. An about eighteen (18) gm sample of filter paper is weighed. After 10 minutes, the 0.5 psi weight is removed from the absorbent core and the filter paper is placed over the sample. The 0.5 psi weight is placed over the filter paper and left for 10 minutes. After 10 minutes, the 0.5 psi weight and the filter paper sample are removed from the absorbent core, and the filter paper is weighed. The Rewet weight is the difference in weight between the dry filter paper and the wet filter paper in gm.

Both the Strikethrough Test and the Rewet Test are measured for a second insult and third insult, each of 100 ml of test solution to the same sample. However, in the second insult rewet procedure, about 50 grams of filter paper are used, and in the third insult rewet procedure, about 72 grams of filter paper are used.

Absorbent Core Manufacture

An absorbent core forming chamber similar to that shown in FIGS. 2 and 3 was operated for approximately 4¾ hours using a range of SAP nozzle configurations instead of a standard SAP nozzle configuration previously used in absorbent core production. The SAP nozzle, made from 304 stainless steel, had an outer diameter of about one and five-sixteenths (1 5/16) inches, with the straight section of the nozzle measuring about twelve (12) inches in length, as depicted by Points B and C in FIG. 1. The curved section of the nozzle had about a seventy (70) degree angle, E in FIG. 1, when measured from a hypothetical plane running parallel to a cross section of the straight section of the nozzle, at the point the nozzle began to curve, to a hypothetical plane running parallel to a cross section at the tip of the nozzle. The curved section of the nozzle protruded for about five and one-half (5½) inches from the point where the nozzle began to curve from the straight section, as measured from Point C in FIG. 1, to a point located in the center of the cross section of the tip of the nozzle, shown by Point D in FIG. 1. The diverter plate was approximately four and three-quarters (4¾) inches long, however only approximately four (4) inches of the diverter plate extended beyond the tip of the nozzle. The funnel was approximately six (6) inches deep, measured between Points A and B in FIG. 1, and was machined to fit inside the straight section of the nozzle, where it was attached by a thumb screw.

The SAP nozzle was placed substantially against a diverter plate when a diverter plate was used. The test was run in a number of configurations, both with the diverter plate bent at different angles with respect to the nozzle tip, and also without the diverter plate in place. In some configurations, the SAP nozzle had a curved lower section and in some configurations the SAP nozzle was straight. Table 1 summarizes the various SAP nozzle configurations used in the test.

TABLE 1

| CODE | NOZZLE | ANGLE OF TOP OF FUNNEL[1] | DIVERTER USED? | LENGTH OF STRAIGHT SECTION OF NOZZLE[2] |
|---|---|---|---|---|
| 1 (Standard) | Straight | 20° | No | SAME |
| 2 | Straight | 20° | Yes | SAME |
| A | Straight | 20° | No | −1 inch |
| B | Straight | 20° | Yes | −1 inch |
| C | Straight | 20° | No | −2 inches |
| E | Straight | 20° | No | −3 inches |
| 3 | Curved | 20° | No | SAME |
| 4 | Curved | 20° | Yes | SAME |
| 5 | Curved | 0° | No | SAME |
| 6 | Curved | 0° | Yes | SAME |
| K | Curved | 0° | No | −1 inch |
| L | Curved | 0° | Yes | −1 inch |
| M | Curved | 0° | No | −2 inches |
| O | Curved | 0° | No | −3 inches |
| Q | Curved | 0° | No | −4 inches |

[1]Angle of funnel is with respect to horizontal, and measured in degrees.
[2]Length of straight section is measured in relation to the standard nozzle.

Samples of a pad of fluff made using each test SAP nozzle configuration were taken, along with samples at the beginning and end of the test under normal operating conditions, and were tested according to the Z-Direction Test Protocol and the Strikethrough Time/Rewet Test Protocol described above in order to screen for absorbent cores that exhibited a good mixture of SAP and fiber, as well as good Strikethrough and Rewet values. Those absorbent cores then would be further tested by making cores in accordance with the codes in Table 1 above, only using a more lengthy core forming procedure to ensure steady state operation, and to more accurately reproduce real-world operating conditions.

In this screening trial, using the Z-Direction Test Protocol, each sample was photographed and examined for distribution of the SAP particles within the fiberized fluff pulp. Samples taken from Codes A, B, C, and L demonstrated the most homogeneous mixture of SAP particles and fiberized fluff pulp. These samples therefore were tested further according to the Strikethrough/Rewet Test Protocol described above, along with the samples using the Code 1 standard SAP nozzle taken at the beginning and end of the test. The results of the Strikethrough test are provided in Table 2, and the results of the Rewet test are provided in Table 3. In the tables, Void 1, Void 2, and Void 3 represent the three insults of 100 ml synthetic urine each.

TABLE 2

| | START SAMPLE | END SAMPLE | CODE A | CODE B | CODE C | CODE L |
|---|---|---|---|---|---|---|
| Void 1 | 26.83 | 23.83 | 25.33 | 28.00 | 28.50 | 22.33 |
| Void 2 | 43.17 | 42.67 | 44.00 | 33.83 | 44.33 | 34.83 |
| Void 3 | 48.17 | 46.50 | 54.33 | 41.83 | 49.00 | 41.00 |
| Std. Dev. of Void 3 | 7.73 | 5.79 | 7.94 | 6.68 | 5.55 | 5.02 |

TABLE 3

| | START SAMPLE | END SAMPLE | CODE A | CODE B | CODE C | CODE L |
|---|---|---|---|---|---|---|
| Void 1 | 0.14 | 0.18 | 0.18 | 0.17 | 0.14 | 0.14 |
| Void 2 | 8.10 | 4.91 | 8.18 | 9.62 | 11.80 | 5.77 |
| Void 3 | 17.93 | 15.55 | 19.09 | 25.27 | 24.12 | 21.18 |
| Std. Dev. of Void 3 | 3.70 | 2.30 | 4.80 | 6.43 | 6.57 | 4.66 |

EXAMPLE 2

Based on the results of the Z-Direction Test Protocol and the Strikethrough/Rewet Test Protocol on the samples in screening Example 1 above, the Code A and Code L SAP nozzle configurations were used to make absorbent cores, only the absorbent cores were made using a more lengthy period of time using the particular nozzle configuration. In addition, two controls were run according to normal operating procedures before and after the new tests using the Code 1 standard SAP nozzle configuration.

Samples from the tests of the Code A and Code L configurations were tested according to the Z-Direction Test Protocol and the Strikethrough/Rewet Test Protocol. The results of the Z-Direction Test Protocol for Code A showed less desirable SAP particle distribution within the fiberized fluff pulp than seen before in Example 1. The Z-Direction Test Protocol results for the Code L configuration were consistent with the prior test in Example 1. The Code L configuration exhibited good SAP distribution within the fiberized fluff pulp as in the trial runs described in Example 1.

The Strikethrough and Rewet test results are shown below in Tables 4 and 5, respectively.

TABLE 4

|  | CONTROL 1 | CONTROL 2 | CODE A | CODE L |
|---|---|---|---|---|
| Void 1 | 29.67 | 28.17 | 30.00 | 28.67 |
| Void 2 | 49.83 | 50.83 | 43.67 | 38.67 |
| Void 3 | 58.17 | 59.00 | 52.50 | 45.83 |
| Std. Dev. of 3d Void | 7.00 | 10.00 | 5.54 | 6.49 |

TABLE 5

|  | CONTROL 1 | CONTROL 2 | CODE A | CODE L |
|---|---|---|---|---|
| Void 1 | 0.32 | 0.19 | 0.15 | 0.17 |
| Void 2 | 9.71 | 7.55 | 2.91 | 1.99 |
| Void 3 | 23.12 | 25.49 | 12.88 | 9.09 |
| Std. Dev. of 3d Void | 6.68 | 3.83 | 3.43 | 1.80 |

As shown in the above tables, the Code L SAP nozzle configuration showed improved distribution of SAP particles and fiber particles, when compared to the controls. In addition, the Code L SAP nozzle configuration also produced a product having improved Strikethrough and Rewet values, when compared to standard SAP nozzle configurations.

EXAMPLE 3

The Code L nozzle configuration was tested again for a ten (10) hour test period. One sample was taken during each hour of the trial, and tested according to the Z-Direction Test Protocol. Again, the Code L configuration exhibited good distribution of the SAP particles in the fiberized fluff pulp in the core. The Strikethrough/Rewet Test Protocol results are given in Tables 6 and 7, respectively for the first sample at hour 1, and the final sample at hour 10.

TABLE 6

|  | FIRST SAMPLE | FINAL SAMPLE |
|---|---|---|
| Void 1 | 29.17 | 30.50 |
| Void 2 | 36.33 | 42.67 |
| Void 3 | 47.83 | 52.50 |
| Std. Dev. of 3d Void | 5.53 | 5.13 |

TABLE 7

|  | FIRST SAMPLE | FINAL SAMPLE |
|---|---|---|
| Void 1 | 0.12 | 0.28 |
| Void 2 | 3.07 | 4.47 |
| Void 3 | 10.36 | 9.48 |
| Std. Dev. of 3d Void | 5.41 | 1.34 |

As shown in the above Tables, absorbent articles made in accordance with the Code L SAP nozzle configuration had improved Strikethrough and Rewet values, when compared to control SAP nozzle configurations.

EXAMPLE 4

Absorbent cores produced from pads of fluff made using the Code A and Code L SAP nozzle configurations were incorporated into training pants, and were tested in Home Use for leakage performance. No control was used in this study. Results of the Home Use Test are provided in Table 8 below, with N defined as the number of samples in which leakage was observed according to the opinion of the observer. The total number of samples tested are noted, (and indicated in the denominator in the table below) as well as a breakdown of the type of usage of the samples when leakage was observed.

TABLE 8

|  | NOZZLE CODE | N BOTH SEXES | % LEAKAGE | N GIRL | % LEAKAGE | N BOY | % LEAKAGE |
|---|---|---|---|---|---|---|---|
| Overall | L | 5/125 | 4.0 | 2/45 | 1.6 | 3/80 | 2.4 |
| Day | L | 3/125 | 2.4 | 1/45 | 0.8 | 2/80 | 1.6 |
| Napping | L | 1/125 | 0.8 | 0/45 | 0.0 | 1/80 | 0.8 |
| Sleeping | L | 1/125 | 0.8 | 1/45 | 0.8 | 0/80 | 0.0 |
| Overall | A | 10/120 | 8.3 | 5/38 | 4.2 | 5/82 | 4.2 |
| Day | A | 2/120 | 1.7 | 0/38 | 0.0 | 2/82 | 1.7 |
| Napping | A | 5/120 | 4.2 | 3/38 | 2.5 | 2/82 | 1.7 |
| Sleeping | A | 3/120 | 2.5 | 2/38 | 1.7 | 1/82 | 0.8 |

The examples above reveal that absorbent cores made using the Code L SAP nozzle configuration can be used to produce absorbent garments having better leakage protection in the Home Use Test than the absorbent garments having cores made using the Code A SAP nozzle configuration.

It is to be understood that the embodiments and variations shown and described herein are merely illustrative of the principles of this invention and that various modifications may be implemented by those skilled in the art without departing from the scope and spirit of the invention.

What is claimed is:

1. An apparatus for dispensing super absorbent particles, comprising:
   a funnel having a first end and a second end, the second end being narrower in diameter than the first end;
   an adjustable nozzle having a straight section, a curved section, and a tip, wherein the straight section of the nozzle is operatively associated with the second end of the funnel, the diameter of said nozzle being adjustable to provide for changes in the flow rate of super absorbent particles; and
   a bent diverter plate operatively associated with the curved section of the nozzle, said diverter plate being bent in the direction of the nozzle at the point of substantial contact between the nozzle tip and the diverter plate.

2. The apparatus of claim 1, wherein the funnel and nozzle are of unitary construction.

3. The apparatus of claim 1, wherein the curved section of the nozzle tapers to form the tip.

4. The apparatus of claim 3, wherein the curve in the curved section of the nozzle is disposed between the straight section of the nozzle and the point in the nozzle wherein the nozzle begins to uniformly decrease in size to form the tip.

5. A system for making an absorbent core, comprising:
a supply of a plurality of fiber sheets;
transport means to transport at least some of the fiber sheets to a fiberizer;
a fiberizer to form fiberized pulp from the fiber sheets;
a gas stream to entrain the fiberized pulp;
a forming chamber with a first end, a midsection, and a second end, wherein the gas stream with the entrained fiberized pulp enters the first end of the forming chamber;
a forming surface located at the second end of the forming chamber, the forming surface comprising a first surface facing the forming chamber, and a second surface facing away from the first surface;
a means for creating a pressure differential between the first surface and the second surface of the forming surface, wherein the pressure on the first surface is higher than the pressure on the second surface; and
an apparatus for introducing super absorbent polymer particles into the midsection of the forming chamber, the apparatus comprising a funnel having a first end and a second end, the second end being narrower in diameter than the first end;
a nozzle having a straight section, a curved section, and a tip, wherein the straight section of the nozzle is operatively associated with the second end of the funnel; and
a diverter plate operatively associated with the curved section of the nozzle.

6. The system of claim 5, wherein the forming chamber further comprises an upper surface and a lower surface, such that the forming surface is housed within the upper surface and the lower surface of the forming chamber.

7. The system of claim 5, wherein the diverter plate extends beyond the tip of the nozzle, and the distance between the point where the diverter plate extends beyond the tip of the nozzle and the forming surface is from about 150 mm to about 205 mm.

8. The system of claim 6, wherein the tip of the nozzle is from about 140 mm to about 160 mm below the upper surface of the forming chamber.

9. The apparatus of claim 5, wherein the tip of the nozzle is substantially in contact with the diverter plate.

10. The apparatus of claim 5, wherein the funnel and nozzle are of unitary construction.

11. The apparatus of claim 5, wherein the curved section of the nozzle tapers to form the tip.

12. The apparatus of claim 11, wherein the curve in the curved section of the nozzle is disposed between the straight section of the nozzle and the point in the nozzle wherein the nozzle begins to uniformly decrease in size to form the tip.

* * * * *